United States Patent [19]
Koike

[11] Patent Number: 5,660,792
[45] Date of Patent: Aug. 26, 1997

[54] AUTOMATIC SOLID PHASE EXTRACTION DEVICE WITH INTERCHANGEABLE NOZZLE HOLDER HEAD

[75] Inventor: Toshio Koike, Kawasaki, Japan

[73] Assignee: Moritex Corporation, Japan

[21] Appl. No.: 569,357

[22] Filed: Dec. 8, 1995

[30] Foreign Application Priority Data

Dec. 12, 1994 [JP] Japan .................... 6-307359

[51] Int. Cl.$^6$ .............................. G01N 1/14; G01N 35/10
[52] U.S. Cl. .................. 422/63; 412/81; 412/100; 412/101; 412/103; 436/43; 436/54; 436/178; 436/180; 73/863.32; 73/864.24; 73/864.25
[58] Field of Search .................. 422/63, 65, 67, 422/81, 101, 100, 103, 104; 436/43, 47, 49, 54, 174, 177, 180, 178; 210/641, 635; 73/864.24, 864.25, 863.32

[56] References Cited

U.S. PATENT DOCUMENTS

| | | | |
|---|---|---|---|
| 5,260,028 | 11/1993 | Astle | 422/81 |
| 5,306,510 | 4/1994 | Meltzer | 422/65 |
| 5,324,480 | 6/1994 | Shumate et al. | 422/63 |
| 5,395,594 | 3/1995 | Nokihara et al. | 422/135 |
| 5,443,791 | 8/1995 | Cathcart et al. | 422/65 |
| 5,525,302 | 6/1996 | Astle | 422/100 |

OTHER PUBLICATIONS

Waters MilliLab™ Workstation brochure, 1989.
BenchMate™ II Workstations brochure, Zymark®, Dec., 1992.

*Primary Examiner*—Long V. Le
*Attorney, Agent, or Firm*—Brown, Martin, Haller & McClain

[57] ABSTRACT

When conducting preprocessing to extract targeted components sample solution, the purpose is to be able to conduct the processing in a shortened length of time by greatly shortening the entire processing time, even if the number being processed is increased. A single needle holder, to which a single needle nozzle is attached to take sample solution into test tubes arranged in a sample rack and inject the sample solution into solid phase extraction tubes, and a multiple linked needle holder for injecting solvent, to which multiple needle nozzles are attached to simultaneously supply multiple solid phase extraction tubes with solvent, are mounted interchangeable on a head, the movement of which can be controlled in the directions of three orthogonal axes; and when aforementioned needle holders are mounted on said head, flow rate control pumps, which are switchable between the intake and discharge directions, are mounted through the piping which connects those needle nozzles with the solvent supply sources.

6 Claims, 3 Drawing Sheets

AUTOMATIC SOLID PHASE EXTRACTION DEVICE WITH INTERCHANGEABLE NOZZLE HOLDER HEAD

BACKGROUND OF THE INVENTION

1. Field of the Invention

This invention is related to an automatic phase extraction device which automatically conducts preprocessing manipulations for analysis of organic chemical components that are contained in drug substances, agricultural chemicals, and water, etc.

2. Description of the Related Art

Liquid chromatography analysis is conducted, for example, to analyze chemical substances that are contained in a sample solution.

This is a device which analyzes components after sample solution has been added by drops from above into a long, cylindrical solid phase extraction tube packed with solid phase adsorption agent. The solute is adsorbed into solid phase, and after preprocessing has been conducted to dissolve out the target components using a solvent flow to separate the solute that has been adsorbed into solid phase, the components are analyzed by placing this in a detector (for example, a differential refraction detector, an ultraviolet absorption detector, an ultraviolet spectrophotometer, or a fluorophotometer).

Then, because it is inefficient to manually conduct these operations which require a great deal of time particularly in preprocessing until the target component is dissolved out, in recent years there have been proposals for devices that automatically conduct these preprocessing manipulations in order to increase processing efficiency.

This is done such that, after sample solution within a test tube has been taken in by a needle nozzle, the position of which has a controllable in 3 orthogonal axes X-Y-Z, and this solution has been injected into a solid phase extraction tube, the eluate which contains the desired components is extracted by adding a solvent by drops into said solid phase extraction tube at a stipulated flow rate.

Because the injection of sample solution and the infusion of solvent into the solid phase extraction tube can all be done automatically, preprocessing up to dissolving out the target component can be conducted without human intervention, and consequently the processing efficiency is greatly improved by, for example, operating day and night.

SUMMARY OF THE INVENTION

Nonetheless, while even this processing efficiency can be improved, for example, by conducting preprocessing while sleeping, because this automatic device can be operated continuously day and night without taking a break, there is the problem that the entire processing time is not greatly different from the manual operation, and processing never stops when the number processed is greatly increased.

Specifically, such operations as conditioning to activate the solid phase within the solid phase extraction tube, injection of the sample solution, washing impurities, extraction of target components, concentration of eluate, and dissolution are conducted as the concrete operations of preprocessing, but because conventional automatic devices repeatedly conduct the independent processing of these operations for each individual solid phase extraction tube, the time required for individual processing is the same as with manual operation if time loss caused by clumsiness and fatigue during manual operation is avoided.

Thus, when executing preprocessing to extract target components from the sample solution, the present invention takes up the technical problem of greatly shortening the entire processing time so that processing can be done even if the number processed is greatly increased.

In order to solve this problem, the present invention involves an automatic solid phase extraction device in which, after sample solution in test tubes arranged within a sample rack has been taken in and injected into solid phase extraction tubes arranged at the stipulated pitch in shift rack, eluate which contains the desired components is extracted by adding a solvent by drops at a specified flow rate into said solid phase extraction tubes; and is characterized by interchangeably mounting on the head, the movement of which can be controlled in 3 orthogonal axes, a single needle holder, to which one needle nozzle is attached to take in one at a time the sample solution in the test tubes that are arranged on the aforementioned sample rack and to inject the sample solution into the solid phase extraction tubes, and the multiple linked needle holder for injecting solvent on which multiple needle nozzles are attached to simultaneously supply the multiple solid phase extraction tubes with solvent; and by providing flow rate control pumps, which can switch between the intake and discharge directions, with tubes which connect those needle nozzles with solvent supply sources when the aforementioned needle holders are equipped on said head.

According to the present invention, activation processing of the solid layer of the solid phase extraction tubes is conducted by first moving the head on which is mounted a multiple linked needle holder for solution injection to the specified test tube position, and simultaneously injecting the specified solvent from the solvent supply source in relation to multiple solid phase extraction tubes by operation of a flow rate control pump.

At this time, for example, if a total of forty solid phase extraction tubes, five longitudinally by eight laterally, are lined up at an equal pitch, the activation processing time can be reduced to $\frac{1}{5}$ because dissolution processing can be conducted simultaneously on five solid phase extraction tubes if using a five linked needle holder on which vie link needle nozzles are attached.

Continuing, a single needle holder is mounted on the head, sample solution within each test tube arranged in the aforementioned sample rack is taken in, and this is injected in the solid phase extraction tubes that have completed activation processing.

In particular, the single needle holder is suitable when it is necessary to precisely control the amount of sample solution injected, and there will be no fluctuations in the amount injected, which is a concern that arises when injecting several simultaneously.

When injecting the sample solution is complete, the multiple linked needle holder is again mounted for injecting the solvent, and the solvent is injected from the solvent supply source to multiple solid phase extraction tubes by operating the flow rate control pump simultaneously with moving the head to the specified test tube position.

In this situation as well, the time of the dissolution process, which requires the most time to conduct, can be shortened because dissolution processing can be conducted on multiple solid phase extraction tubes simultaneously, and consequently the entire processing time is markedly shortened.

BRIEF DESCRIPTION OF THE DRAWINGS

Below, the present invention will be specifically explained based on the embodiments indicated in the diagrams.

DETAILED DESCRIPTION OF THE PREFERRED EMBODIMENTS

Figure 1:
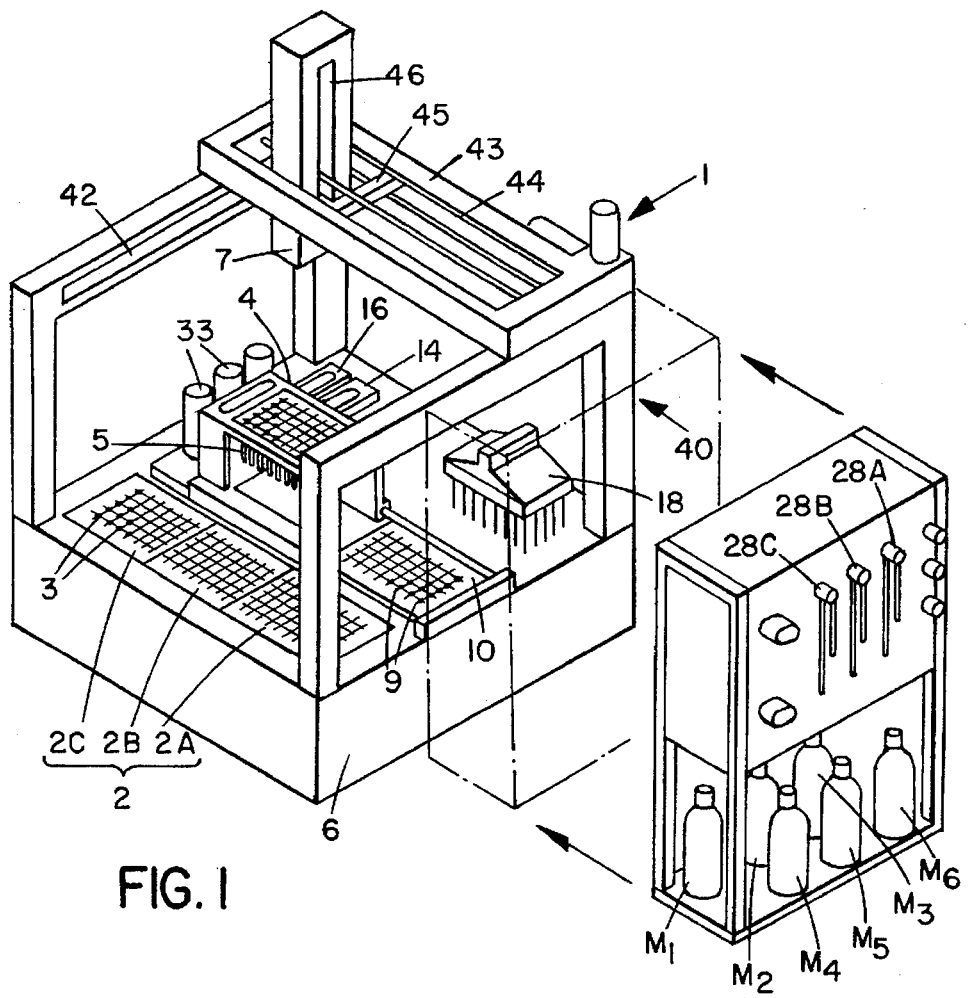
FIG. 1 is a perspective diagram of a solid phase extraction device relating to the present invention.
Figure 2:
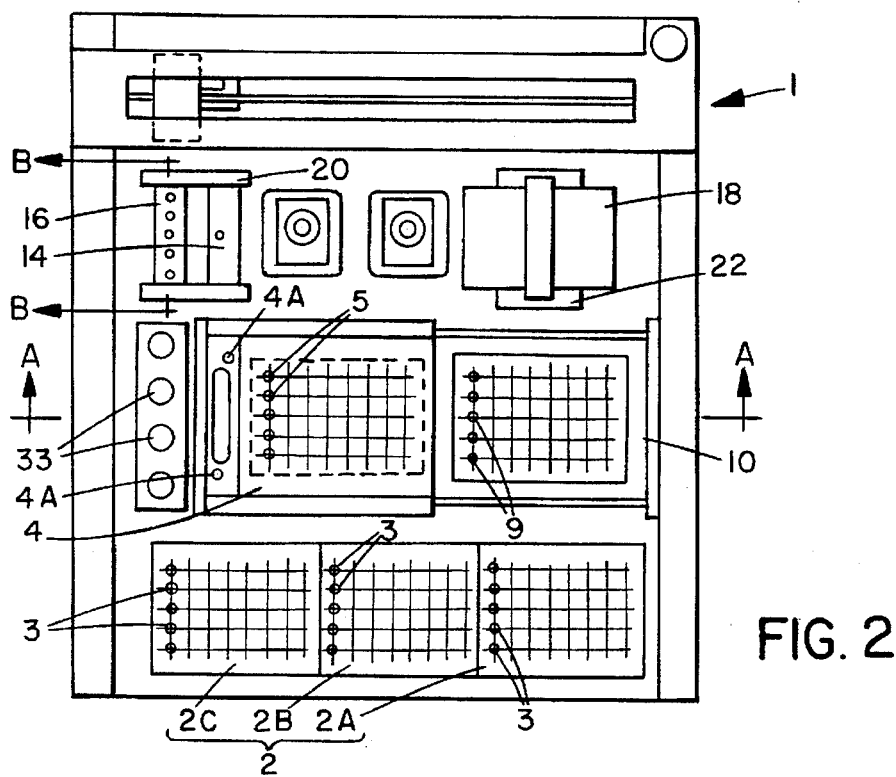
FIG. 2 is a top view of the same.
Figure 3:
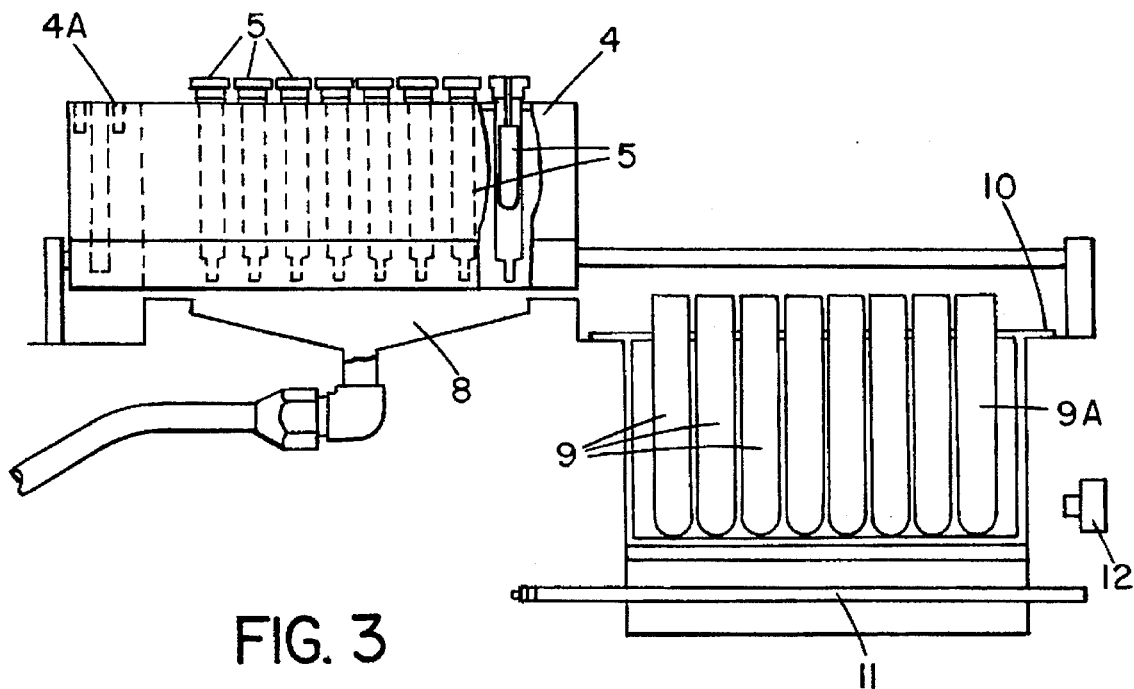
FIG. 3 is a cross-sectional diagram along the A—A line in FIG. 2.

In the diagram, 1 is an automatic solid phase extraction device which, after taking in sample solution in test tubes 3 arranged in sample rack 2 and injecting this into solid phase extraction tubes 5 arranged in a grid at a specified pitch within shift rack 4, the eluate which contains the desired component is extracted by adding solvent by drops at a specified flow rate simultaneously into multiple solid phase extraction tubes 5. The device is provided with a support frame 6 having a base portion on which the racks 2,4 are mounted as illustrated, and an upper support portion 40 from which a pick up head 7 is movably suspended. Support portion 40 has a first slide rail or track 42 extending in a first direction, and a first sliding carriage or support member 43 is movable along track 42 in a first or x-direction. Support member 43 has a second slide rail 44 extending perpendicular to rail 42 in a second or y-direction, and a second sliding carriage 45 is slidably mounted on rail 44 as illustrated in FIG. 1. Pick up head 7 has a vertical or z-direction slide rail or slot 46 which engages carriage 45 for vertical movement of head 7. Head 7 is therefore movable in three orthogonal directions by means of suitable drive mechanisms (not illustrated) in a manner which will be understood by one skilled in the field.

Aforementioned shift rack 4, for example, organizes a total of forty, five longitudinally and eight latitudinally, solid phase extraction tubes 5 at a specified pitch, and is installed between the wash position on the left side and the dissolution position on the right side such that it is slidable horizontally; there are engagement holes 4a which engage with pins 7a that protrude from head 7, and shift rack 4 is moved by moving head 7 to the left and right along rail 44 when engagement holes 4a are made to engage with those pins 7a.

Moreover, formed in the aforementioned wash position is drain pan 8, which recovers waste solution that has flowed from solid phase extraction tubes 5; and provided on the aforementioned dissolution side is fraction rack 10, in which test tubes 9 which recover the eluate that is dissolved from solid phase extraction tubes 5 are arranged in a 5×8 grid at the same pitch as solid phase extraction tubes 5.

Then, provided within fraction rack 10 is heater 11, which heats test tubes 9 to the specified temperature; and CCD camera 12 is arranged facing the side of test tube 9a to monitor the fluid level.

Moreover, sample rack 2 is provided, for example, with original solution rack 2A which arranges into a 5×8 grid test tubes 3 containing original sample solution; dissolution rack 2B which arranges into a 5×8 grid test tubes 3 containing dilute sample solution in which original sample solution is thinned to a specified magnification; and adjustment rack 2C which arranges into a 5×8 grid test tubes 3 containing sample solution which has been PH adjusted. These are lined up respectively in front of shift rack 4.

Formed on aforementioned head 7 is connector 19 on which is installed in a freely mountable/removable way: single needle holder 14 on which is attached a single needle nozzle 13 which individually takes in the test solution within test tubes 3 arranged on aforementioned sample rack 4 and injects the sample solution into solid phase extraction tubes 5; multiple linked needle holder 16 for solvent injection on which are attached five needle nozzles 15 to supply solvent simultaneously to five solid phase extraction tubes 5 lined up in a row; and multiple linked needle holder 18 for evaporation to dryness on which is attached multiple needle nozzles 17 which simultaneously blow in pressurized gas in relation to all test tubes 9 of fraction rack 10. Each of these needle holders 14,16 and 18 can be suitably mounted in an interchangeable manner.

Figure 4:
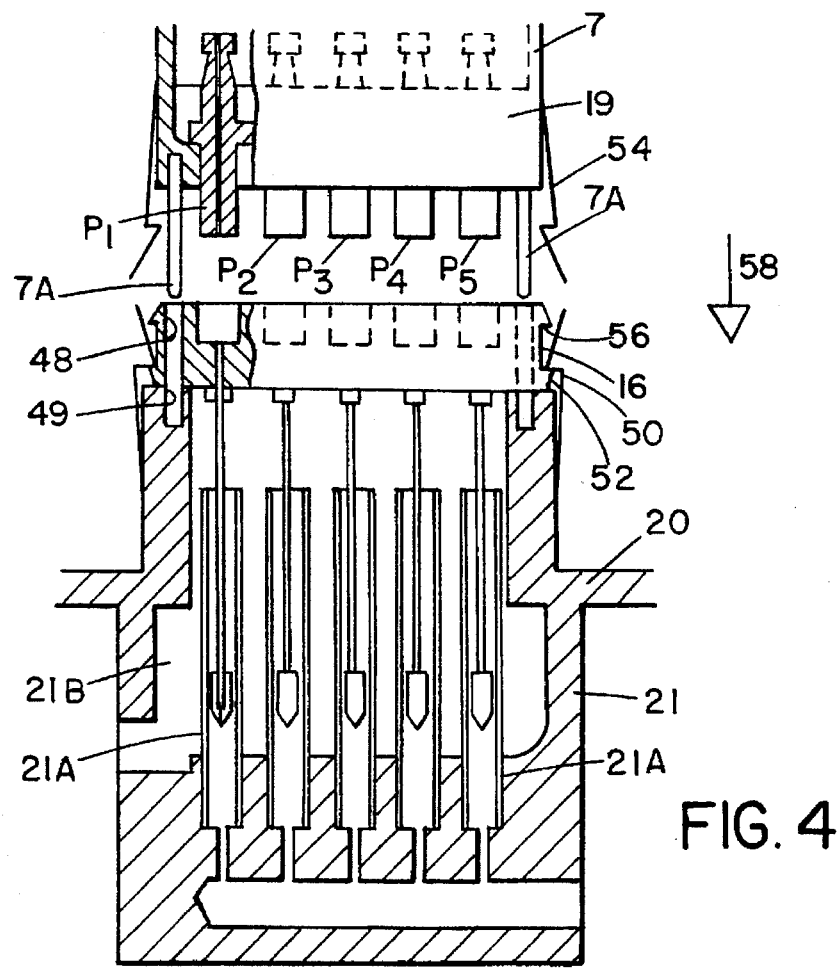
FIG. 4 is a cross-sectional diagram along the B—B line in FIG. 2 with the pick up head positioned vertically above a needle holder.
Figure 5:
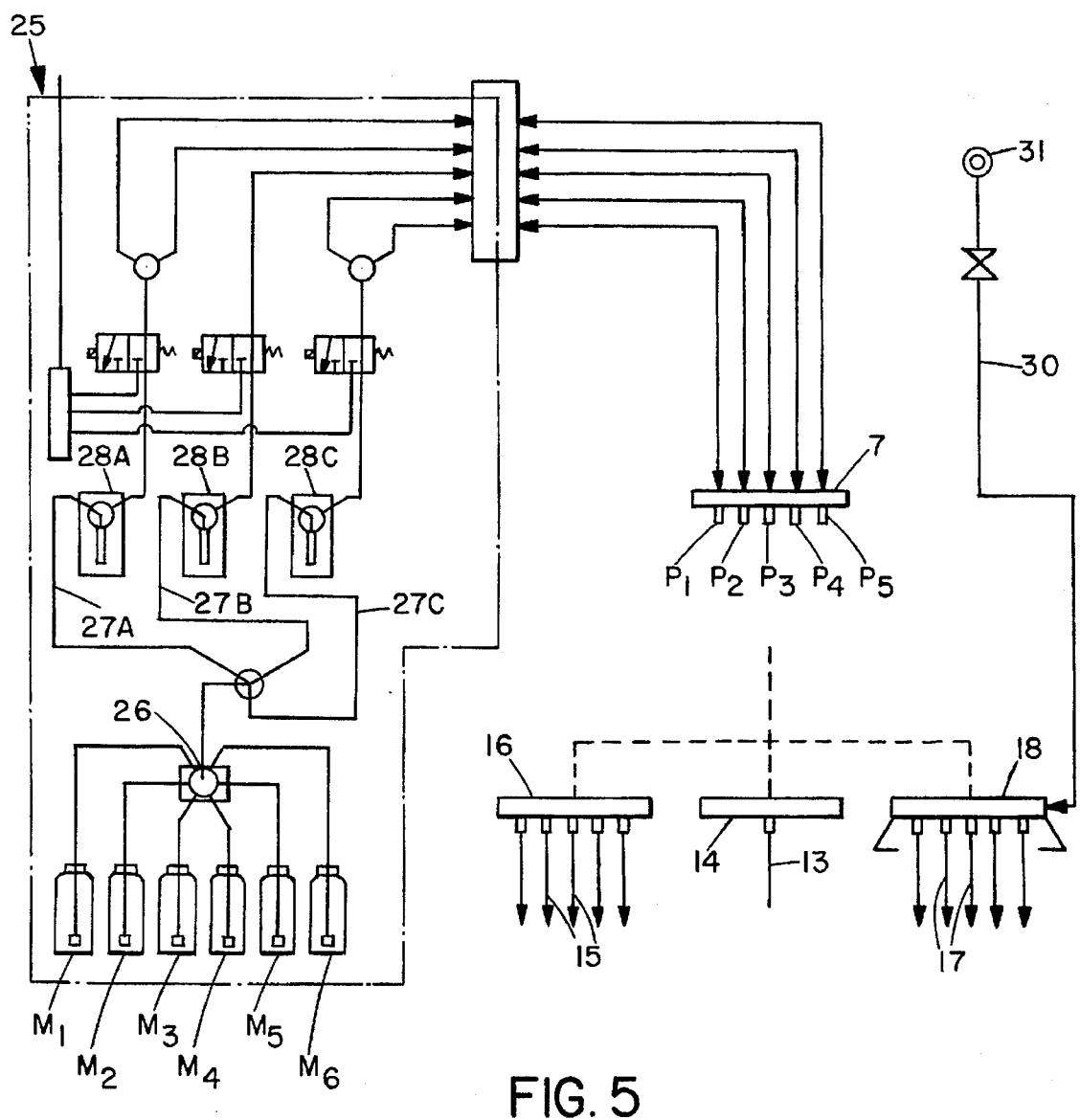
FIG. 5 is a flow sheet indicating the piping system.

FIG. 4 illustrates head 7 located vertically above needle holder 16 after appropriate positioning along the x and y axes. As illustrated, pins 7a which project downwardly from head 7 are aligned with holes or bores 48 in needle holder 16 and aligned bores 49 in the receiving rack. It will be understood that similar bores 48 will be provided in needle holders 14 and 18. At initial start up, each of the needle holders 14,16 and 18 is fixed on the receiving rack by means of a receiving clamp or spring clip 50 which engages over a rim or lip 52 along the lower edge of the respective needle holder, as illustrated in FIG. 4 for the needle holder 16. The pick up head 7 has a downwardly projecting pusher clamp or spring clip 54 for engagement over a rim or lip 56 along the upper edge of each needle holder. As the head 7 is moved downwardly in the direction of the arrow 58 in FIG. 4, the end of clamp 54 engages clamp 50 and forces it outwardly to release the needle holder. At the same time, clamp 54 snaps over rim 56 and the needle holder 16 is releasably secured to the movable head 7, so that it can be carried by the head to a desired location, as described in more detail below.

When a needle holder is returned to its receiving rack 20, the end of clamp 50 will engage clamp 54 as the head 7 moves downwardly, forcing clamp 54 outwardly to release the needle holder. The clamp 50 then moves back into the position illustrated in FIG. 4.

20 is a reception rack which provides washing device 21 that washes needle nozzles 13 and 15 of single needle holder 14 and multiple linked needle holder 16 for injecting solution, and is formed to the left-hand side in the rear; and when needle holders 14 and 16 are not being used, these are removed from head 7 and are placed on said receiving rack 20.

Also, it is not necessary to wash multiple linked needle holder 18 for evaporation to dryness because only pressurized gas is supplied. Consequently, this is placed on receiving rack 22 which is on the right-hand side to the rear, and is not equipped with a washing device.

Washing device 21 is formed by arranging washing pipe 21A in washing tank 21B to supply washing solution from the lower side.

Then, when washing needle nozzles 13 and 15, if needle holders 14 and 16 are placed on receiving rack 20 installed on head 7 as is, needle nozzles 13 and 15 are inserted in wash pipe 21A, and their exteriors are washed by washing solution within washing pipe 21B, and their insides are washed by discharging a solvent from needle nozzles 13 and 15.

Piping system 25 is a device which, when aforementioned single needle holder 14 is mounted on head 7, is for the purpose of taking in and discharging sample with that needle nozzle 13; and which, when multiple linked needle holder 16 is mounted, is for the purpose of injecting sample and solvent with those needle nozzles 15. Six-way selection valve 26 which switches between six solvent bottles $M_1-M_6$ (solvent supply source) is connected to one side; and on route, the pipe branches to three pipes 27A, 27B and 27C.

Then, digital control syringe pumps 28A, 28B and 28C are mounted through these pipes 27A, 27B and 27C respectively as flow rate control pumps that can switch in the intake and discharge directions; pipes 27A and 27C are further branched into two to form five connection ports $P_1-P_5$; and central connection port $P_3$ is connected to that needle nozzle 13 and the other connection ports $P_1$, $P_2$, $P_4$, and $P_5$ are blocked when single needle holder 14 is mounted on head 7; and all of the connection ports $P_1-P_5$ are connected to needle nozzles 15 when multiple linked needle holder 16 for injecting solvent is mounted on head 7.

Moreover, 30 is a pressurized gas supply pipe for the purpose of supplying pressurized air and nitrogen gas from pressurized gas supply source 31 in relation to multiple linked needle holder 18 for evaporation to dryness which is mounted on head 7.

Furthermore, 33 is a solvent vial containing the necessary solvent other than the solvent which is supplied from solvent bottles $M_1-M_5$, and is used by being taken in by needle nozzle 13 of single needle holder 14 as necessary when adjusting the sample.

The foregoing was the structure of the present invention, and its action will now be explained in the following.

First, test tubes 3 containing original sample are arranged in original sample rack 2A, and sample preparation is conducted such as dilution processing and PH adjustment as necessary.

When sample preparation is conducted, single needle holder 14 is used because of the rigorous standards required for the amount of sample solution taken in and injected, and for the amount of solvent injected.

Then, using syringe pump 28B which is mounted through piping 27B, the specified solvent among solvent bottles $M_1-M_6$ is supplied, and filled up to the tip of needle nozzle 13.

Continuing, head 7 is moved, needle nozzle 13 is inserted inside test tube 3 of original sample rack 2A, syringe pump 28B is switched to the intake side, an air layer is inserted, and original sample solution from test tube 3 of rack 2A for original sample is taken in only to the specified amount.

Then, needle nozzle 13 is extracted, head 7 is again moved, and at this time is inserted in test tube 3 of sample rack 2B, and only the sample solution taken into needle nozzle 13 is injected into test tube 3 by switching syringe pump 28B to the supply side and feeding solvent into piping 27B.

Furthermore, each time injection is completed, needle nozzle 13 is washed by washing device 21, and original sample solution is injected one by one into test tubes 3 arranged on dilution rack 2B.

Each time injection of original sample solution into a test tube 3 of dilution rack 2B is complete, it is diluted to the specified magnification by supplying diluent.

In this situation, for example, if dilution solvent contained in solvent holder $M_1$ is used, solvent holder $M_1$ is selected by six-way selection valve 26, syringe pump 28B is switched to the supply side, and the specified amount of that solvent is injected in each test tube 3 of dilution rack 2B.

Moreover, if the solvent within solvent vial 33 is used as the dilution solvent, the specified amount is taken from solvent vial 33 using needle nozzle 13, and this is injected into test tube 3 of dilution rack 2B.

In addition, the sample solutions in test tubes 3 are agitated as necessary at this time. This is conducted by injecting diluent with the tip of single needle 13 inserted below the liquid surface of the sample solution in test tube 3, and after dilution processing has been completed, the tip of single needle 13 is inserted below the liquid surface of the dilute sample solution in test tube 3 and the dilute sample solution inside test tube 3 is repeatedly taken in and discharged.

When sample preparation has been completed in this way, conditioning is executed in which the solid phase is activated within solid phase extraction tubes 5 arranged in shift rack 4.

This is activated by bring shift rack to the washing position on the left side, mounting on head 7 multiple linked needle holder 16 for injecting solvent, and injecting the specified activation solvent that is supplied from syringe pumps 28A-28C into the five solid phase extraction tubes 5 that are arranged in a row.

When it is not necessary to strictly control the amount of solvent, etc. supplied in this way, the processing time can be shortened as a whole because multiple (in this example five) solid phase extraction tubes 5 are simultaneously processed using multiple linked needle holder 16 for injecting solvent.

When conditioning is completed, single needle holder 14 is mounted on head 7, and sample loading is conducted by injecting into solid phase extraction tube 5 the desired sample solution that has been taken in only to the specified amount from test tube 3 of sample rack 2.

At this time, for example, when the original sample solution is used as is, head 7 is moved such that the original sample solution taken from test tube 3 of original sample rack 2A is injected into solid phase extraction tube 5; and when using dilute sample solution, head 7 is moved such that dilute sample solution which his been taken from test tube 3 of dilution rack 2B is injected.

Moreover, after injecting the sample solution into solid phase extraction tube 5, needle nozzle 13 is washed every time, and the admixture of sample solutions is prevented.

When sample loading is complete, the washing manipulation to rinse away impurities that are maintained in the solid phase of solid phase extraction tubes 5 is conducted.

This is conducted by mounting on head 7 multiple linked needle holder 16 for injecting solvent in the same way as during conditioning, and injecting rinse solvent.

At this time, the solution which is washed away from solid phase extraction tubes 5 is recovered by drain pan 8 and drained to the outside.

When the washing operation is complete, this time a dissolution operation is conducted in which the target component is dissolved by injecting a solvent into solid phase extraction tube 5.

First, shift rack 4 is positioned in the dissolution position by fitting pins 7a of head 7, on which needle holder 16 is still mounted, into engagement holes 4a of shift rack 4, and moving as is to the right side.

Then, head 7 is positioned in the specified position, the dissolution operation is conducted simultaneously on 5 solid phase extraction tubes by injecting the desired solvent at the specified amount of injection, and recovering the eluate that is dissolved from solid phase extraction tubes 5 into test tubes 9 of fraction rack 10.

This dissolution processing requires the most time, but the entire processing time can be shortened compared to conventional processing because dissolution processing can be simultaneously conducted on multiple solid phase extraction tubes.

In addition, when changing the kind of solvent supplied from solvent bottles $M_1-M_6$, solvents that differ inside the piping are kept from mixing by the fact that all of the previous solvent packed in piping 27A–27C is washed through into washing tank 22.

Then, when dissolution processing of all the solid phase extraction tubes 5 is complete, this time, the operation of concentrating the eluate recovered in test tubes 9 of fraction rack 10 is conducted as necessary.

At this time, after shift rack is moved to the left side with head 7, multiple linked needle holder 18 for evaporation to dryness is first mounted on head 7, nitrogen replacement is conducted by supplying nitrogen gas into all test tubes 9 within fraction rack 10, and the eluate is heated by heater 11 as necessary.

At this time, because the liquid level position of test tubes 9 is monitored by CCD camera 12, if the liquid level position when concentrating to an optional concentration is set ahead of time and processing is automatically stopped when the set surface level position and the surface level position detected by CCD camera 12 agree, the concentration operation can be automatically completed when reduced to the set liquid level position, that is, when concentrated to the optional concentration. Thus, it is not at all necessary to monitor the liquid level position of test tubes 9 with constant human attendance.

Then, when the concentration operation is complete, this is again dissolved by injecting dissolution liquid into test tubes 9 as necessary, and processing is complete by further dilution.

In addition, multiple linked needle holder 16 for injecting solvent is not limited to installing five needle nozzles 15, and can be set optionally corresponding to the numeric arrangement of solid phase extraction tubes 5, etc.

Moreover, multiple linked needle holder 18 for evaporation to dryness is not limited to supplying nitrogen gas, etc. simultaneously in relation to all test tubes 9 arranged in fraction rack 10, and it is also possible, for example, to be combined with multiple linked needle holder 16 for injecting solvent to which five needle nozzles 15 are attached.

In addition, the invention is not limited to when using digital control syringe pumps 28A, 28B, and 28C as the flow rate control pumps capable of switching in the inlet and discharge directions, and high pressure plunger pumps and other pumps can be used.

Furthermore, in this embodiment, the explanation was given when injecting sample solvent into the solid phase extraction tubes using single needle holder 14, but when it is not necessary to control the amount of injection that rigorously, injecting sample solvent may also be done with multiple linked needle holder 16 for solvent injection.

As described above, according to the present invention, because, when conducting operations which require rigorous quantitative characteristics such as taking in and injecting sample solution, one test tube at a time is processed by mounting on the head a single needle holder to which one needle nozzle is attached, and when conducting operations which to not require that degree of rigorous quantitative characteristics such as the dissolution operation, can process multiple test tubes simultaneously by supply solvent to multiple solid phase extraction tubes simultaneously by mounting on the head a multiple linked needle holder to which multiple needle nozzles are attached. Thus, there is the superior effect that the entire processing time can be greatly reduced without losing reproducibility.

Although some preferred embodiments of the invention have been described above by way of example only, it will be understood by those skilled in the field that modifications may be made to the disclosed embodiments without departing from the scope of the invention, which is defined by the appended claims.

I claim:

1. Automatic solid phase extraction apparatus, comprising:
   a support frame having a base and an overhead support spaced above the base;
   a sample rack at a first position in the base underlying the overhead frame, a first set of test tubes arranged in said sample rack;
   a shift rack mounted in a second position in the base for supporting solid phase extraction tubes arranged at a predetermined pitch in the shift rack;
   an x-, y- and z-direction transport mechanism mounted on said overhead support;
   a head adjustably mounted on said transport mechanism for movement in three orthogonal directions relative to said base;
   a single needle holder removably supported on the base, a single needle nozzle attached to said needle holder for receiving sample solution one at a time from said first set of test tubes arranged in said sample rack and for injecting sample solution into said solid phase extraction tubes on said shift rack;
   a multiple linked needle holder removably mounted on said base, a plurality of needle nozzles attached to said multiple linked needle holder for simultaneously supplying said solid phase extraction tubes with solvent;
   said head having engaging means for releasably engaging a selected needle holder and transporting said needle holder to a selected rack; and
   said head having a plurality of flow rate control pumps for alignment with respective needle nozzles when a respective needle holder is secured to said head for supplying solvent to said needle nozzles, each flow rate control pump being switchable between intake and discharge directions.

2. The apparatus as claimed in claim 1, further comprising a fraction rack located at a third position in the base, a second set of test tubes supported in said fraction rack for recovering eluate from the solid phase extraction tubes, and a second multiple linked needle holder removably mounted on the base, the second multiple linked needle holder having a plurality of needle nozzles for injecting pressurized gas into the second set of test tubes of said fraction rack, and the head engaging means further comprising means for releasably engaging said second multiple linked needle holder.

3. The apparatus as claimed in claim 2, wherein said fraction rack is located below said shift rack, and said shift rack is horizontally movable between a wash position offset to one side of said fraction rack and a dissolution position located vertically above said fraction rack with said solid phase extraction tubes aligned with the second set of test tubes in said fraction rack.

4. The apparatus as claimed in claim 2, including a pressurized gas supply and piping connecting said gas supply to the needle nozzles of the second multiple linked needle holder when said second needle holder is engaged with said head.

5. The apparatus as claimed in claim 2, including a heater mounted in the fraction rack for heating the second set of test tubes to a predetermined temperature.

6. The apparatus as claimed in claim 2, wherein said second set of test tubes each have a closed bottom, an open top, and elongate sides, and a CCD camera is positioned adjacent said fraction rack facing the sides of the test tubes for monitoring liquid level in said second set of test tubes of said fraction rack.

* * * * *